US00PP32272P3

(12) United States Plant Patent
Xingfu et al.

(10) Patent No.: US PP32,272 P3
(45) Date of Patent: Oct. 6, 2020

(54) POPLAR TREE NAMED 'GOLD POPLAR'

(50) Latin Name: *Populus*
Varietal Denomination: Gold Poplar

(71) Applicant: Changchun Senfeng Agroforestry Technology Development Co., Ltd., Huadian (CN)

(72) Inventors: Wang Xingfu, Huadian (CN); Wang Xiaoduo, Huadian (CN)

(73) Assignee: Changchun Senfeng Agroforestry Technology Development Co., Ltd., Huadian, Jilin Province (CN)

( * ) Notice: Subject to any disclaimer, the term of this patent is extended or adjusted under 35 U.S.C. 154(b) by 0 days.

(21) Appl. No.: 16/501,288

(22) Filed: Mar. 19, 2019

(65) Prior Publication Data

US 2019/0307038 P1 Oct. 3, 2019

(30) Foreign Application Priority Data

Mar. 29, 2018 (CN) ..... 20180185

(51) Int. Cl.
*A01H 5/00* (2018.01)
*A01H 6/00* (2018.01)
*A01H 5/04* (2018.01)

(52) U.S. Cl.
USPC ..... Plt./218
CPC ..... *A01H 6/00* (2018.05); *A01H 5/04* (2013.01)

(58) Field of Classification Search
USPC ..... Plt./218
CPC ..... A01H 5/00; A01H 6/00
See application file for complete search history.

*Primary Examiner* — Keith O. Robinson
(74) *Attorney, Agent, or Firm* — Knobbe, Martens, Olson & Bear, LLP

(57) ABSTRACT

A new and distinct poplar tree variety, *Populus*, cv. 'Gold Poplar' is characterized by having tender yellow color leaves in the spring (Y100,C10,M5,B0), green and yellow leaves in the summer (Y100,C20,M10,B0) and gold leaves in the fall (Y100,C0,M40,B0) with a red petiole (Y100,M100,C20, B0).

8 Drawing Sheets

Latin name of the genus claimed: *Populus*.
Variety denomination: 'Gold Poplar'.

REFERENCE TO RELATED APPLICATIONS

The present application claims the benefit under 35 U.S.C. § 119(c) of Chinese PBR Application No. 20180185, filed Mar. 29, 2018, which is incorporated herein by reference in its entirety under 37 C.F.R. § 1.57.

BACKGROUND AND SUMMARY OF THE INVENTION

This application relates to the discovery and asexual propagation of a new and distinct variety of *Populus* cv. 'Gold Poplar'. The new variety was found in July 2011 among 'Xiao Hei Yang' trees (*Populus* X *xiaohei*) that were planted in Ba dao he zi Village, Huadian, Jili City, Jilin Province, China. The new variety is believed to be a mutation derived from the parent 'Xiao Hei Yang' trees. The new variety was discovered and asexually propagated by Wang Xingfu and Wang Xiaoduo and after observation to confirm stable and consistent traits was given the name of 'Gold Poplar' in 2017.

The new variety 'Gold Poplar' has been shown to maintain its distinguishing characteristics through successive asexual propagations by, for example, cuttings. Spikes of the new variety 'Gold Poplar' were collected in June 2012, from which more than 100 seedlings were cultivated using the method of twig cuttings. The resulting spikes were collected in December 2012 and in the spring of 2013 more than 800 seedlings were planted. By 2017 more than 80,000 seedlings were bred. Trees of the new variety have moderate growth, strong cold resistance and excellent ornamental properties, with leaves having a golden color in the fall. It was observed that the traits were stable and consistent throughout multiple generations and over many years.

The characteristic which distinguishes the new variety from other known poplar varieties is the leaf color. The new variety 'Gold Poplar' has tender yellow colored leaves in the spring, yellow green colored leaves in the summer and gold colored leaves in the fall, with a red petiole.

The new variety 'Gold Poplar' differs from 'Xiao Hei Yang' (*Populus* X *xiaohei*) (unpatented) and 'Qing Yang' (*Populus cathayana*) (unpatented) in that the new variety has a tender yellow leaf color in the spring and yellow green leaf color in the summer while the two comparative varieties have green color leaves in both spring and summer. Additionally, the new variety 'Gold Poplar' has a golden color leaf in the fall, while 'Xiao Hei Yang' (*Populus* X *xiaohei*) and 'Qing Yang' (*Populus cathayana*) have yellow-colored leaves in the fall.

The new variety 'Gold Poplar' has the same range of day-time growing temperatures as other common outdoor *Populus* cultivars.

BRIEF DESCRIPTION OF THE PHOTOGRAPH

The accompanying photographs show typical specimens of the new variety, designated 'Gold Poplar' in the illustrations, including foliage, trunk and stems, in color as nearly true as it is reasonably possible to make in color illustrations of this character.

The photographs of the new variety 'Gold Poplar' were taken in China in 2017 and 2018.

DESCRIPTION OF THE NEW VARIETY

Figure 1:
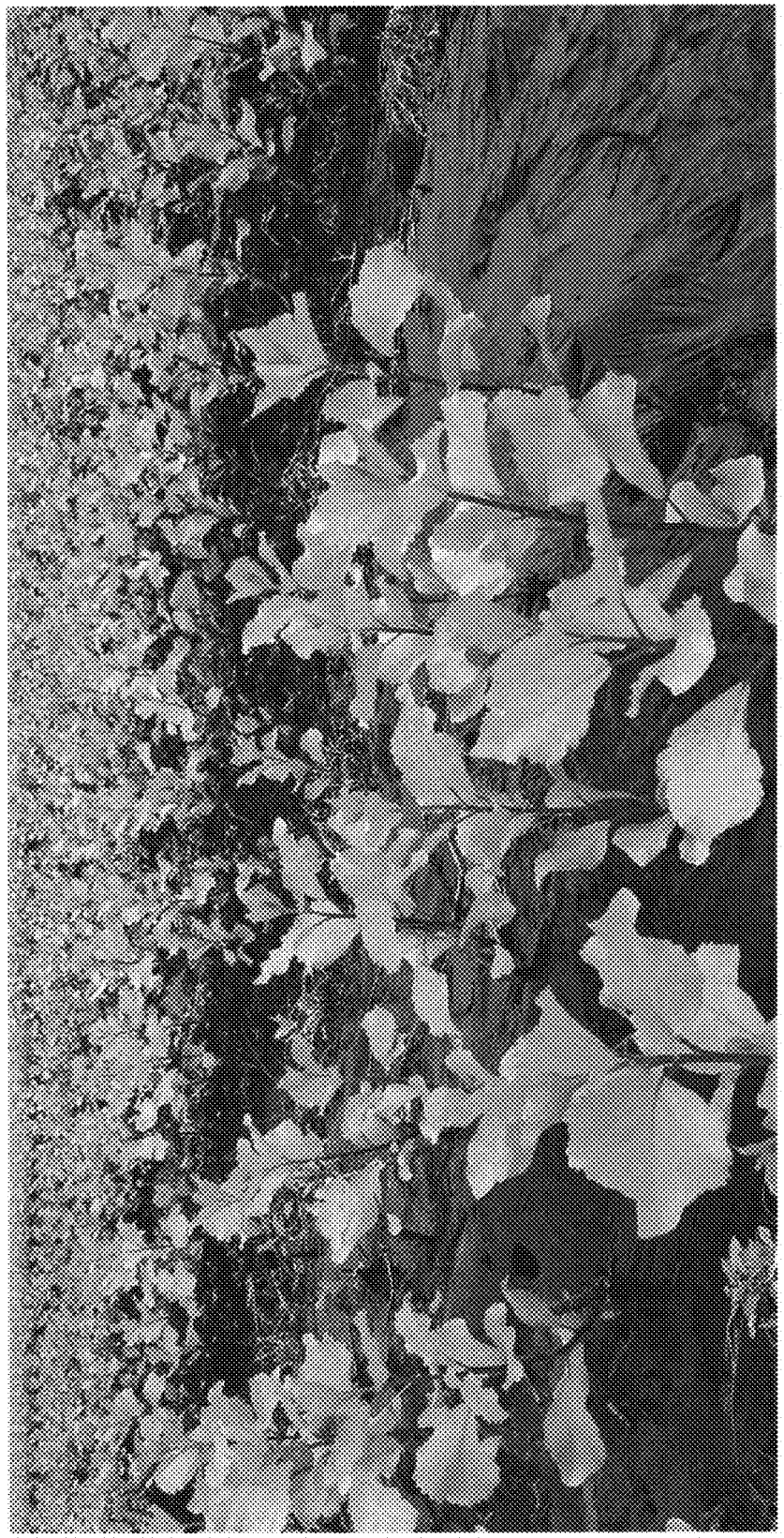
FIGS. 1 and 2 show one-year-old trees with two-year-old roots and one-year-old stems of the new variety 'Gold Poplar' in the summer of 2018 in Huadian, Jilin, China.
Figure 2:
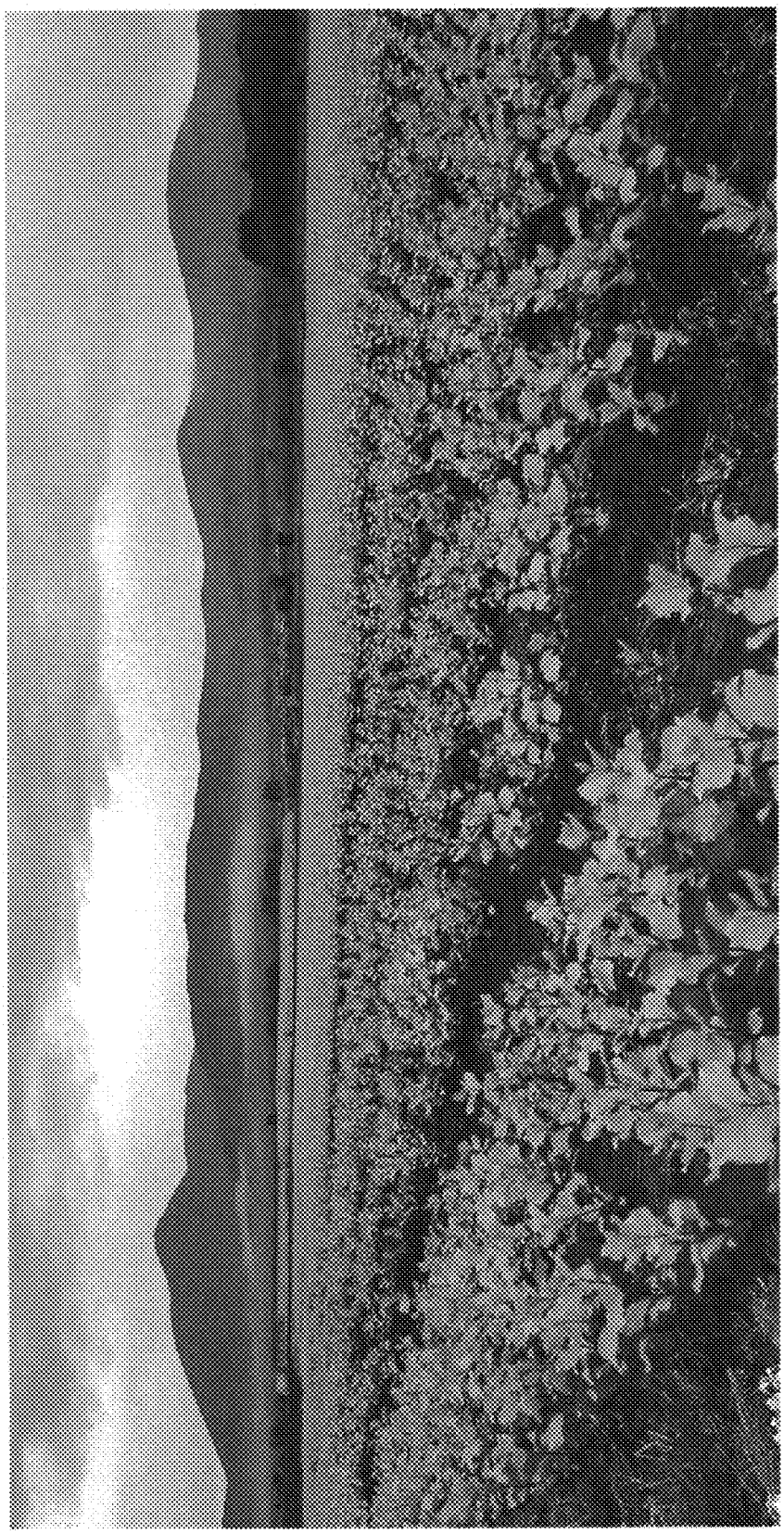
Figure 3:
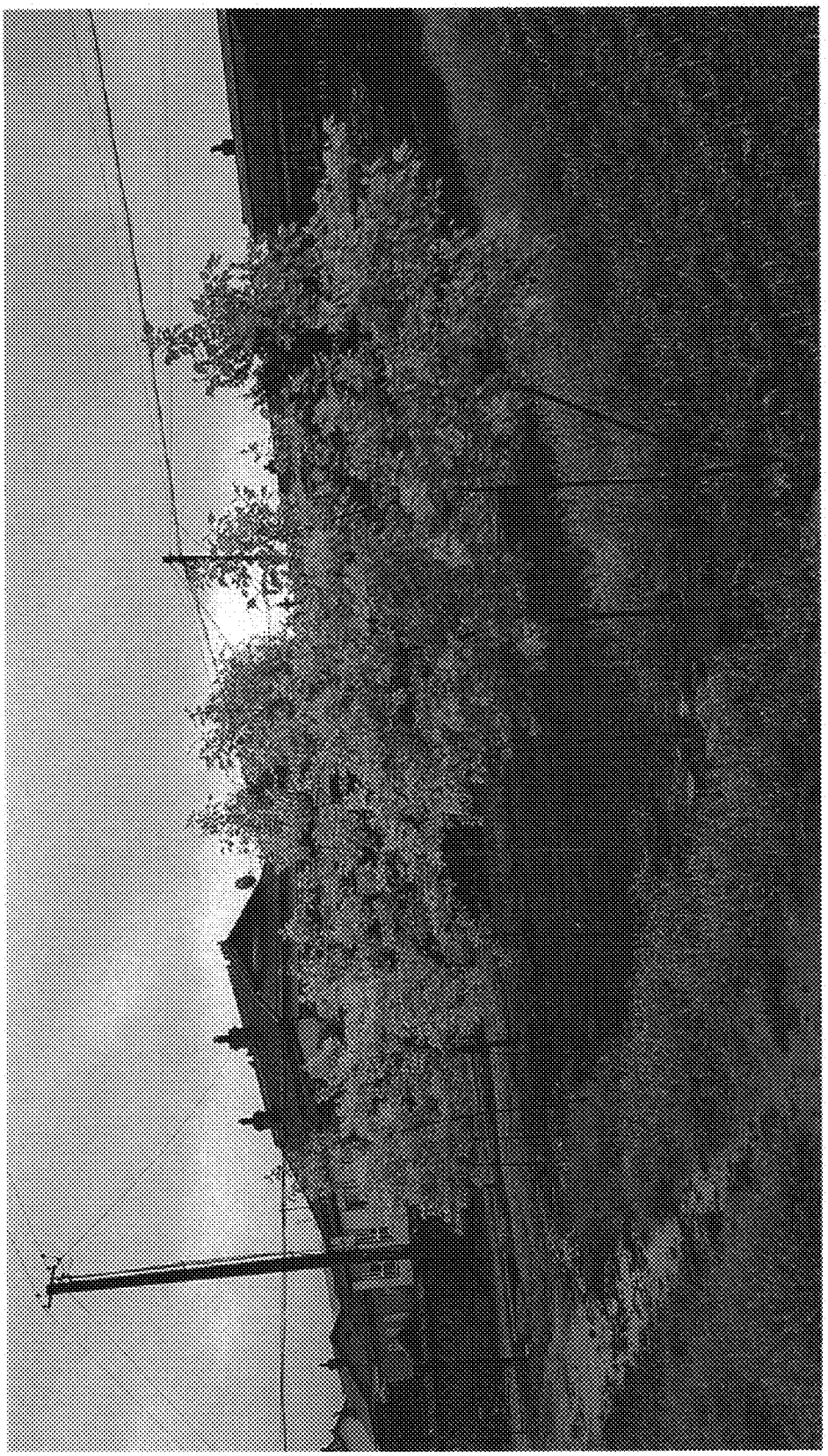
FIG. 3 shows three-year-old trees with three-year-old roots and three-year-old stems of the new variety 'Gold Poplar' in the summer of 2018 in Huadian, Jilin, China.
Figure 4:
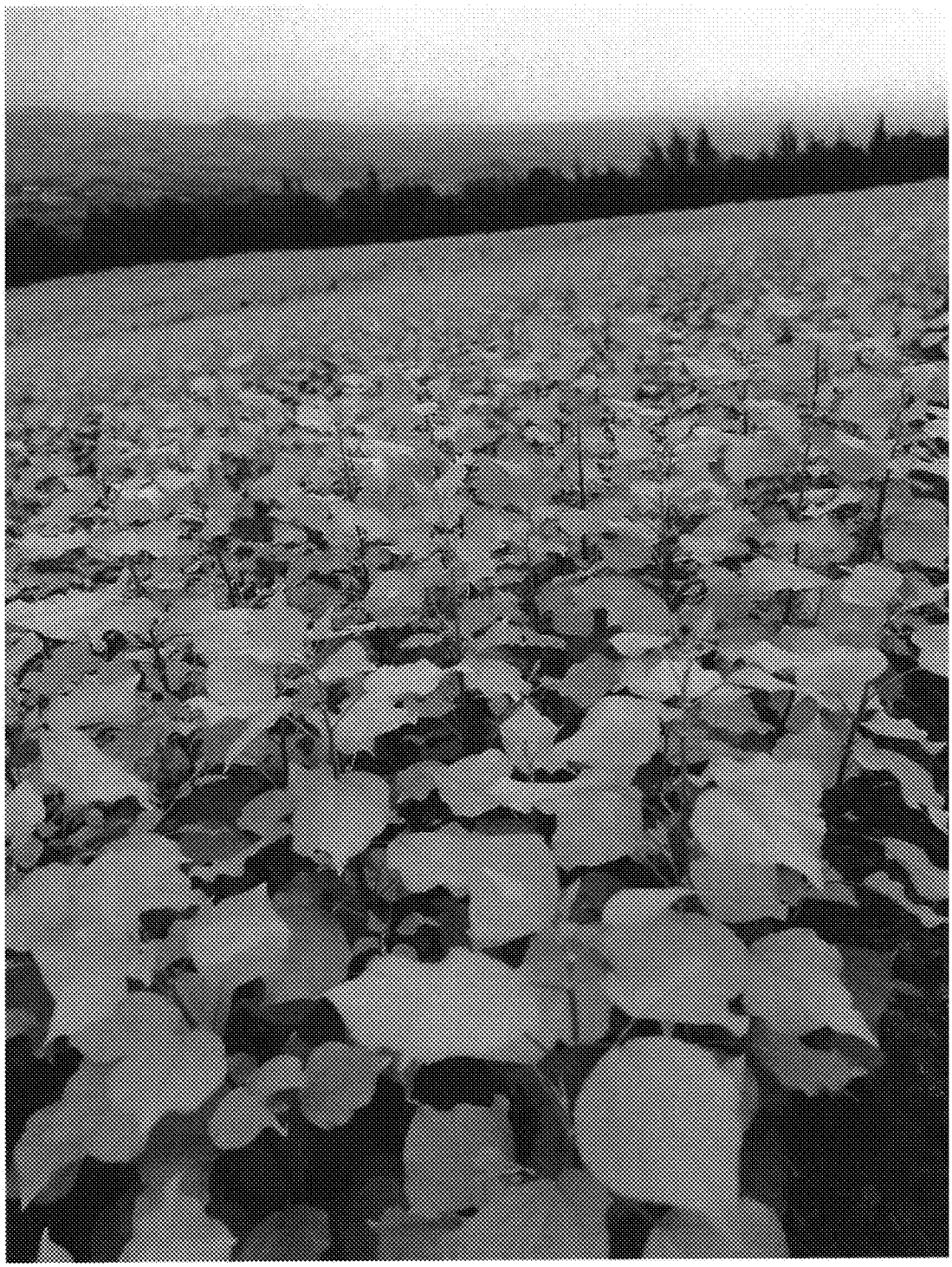
FIGS. 4, 5 and 6 show one-year-old trees with one-year-old roots and one-year-old stems of the new variety 'Gold Poplar' in the summer of 2018 in Longtan, Jilin, China.
Figure 5:
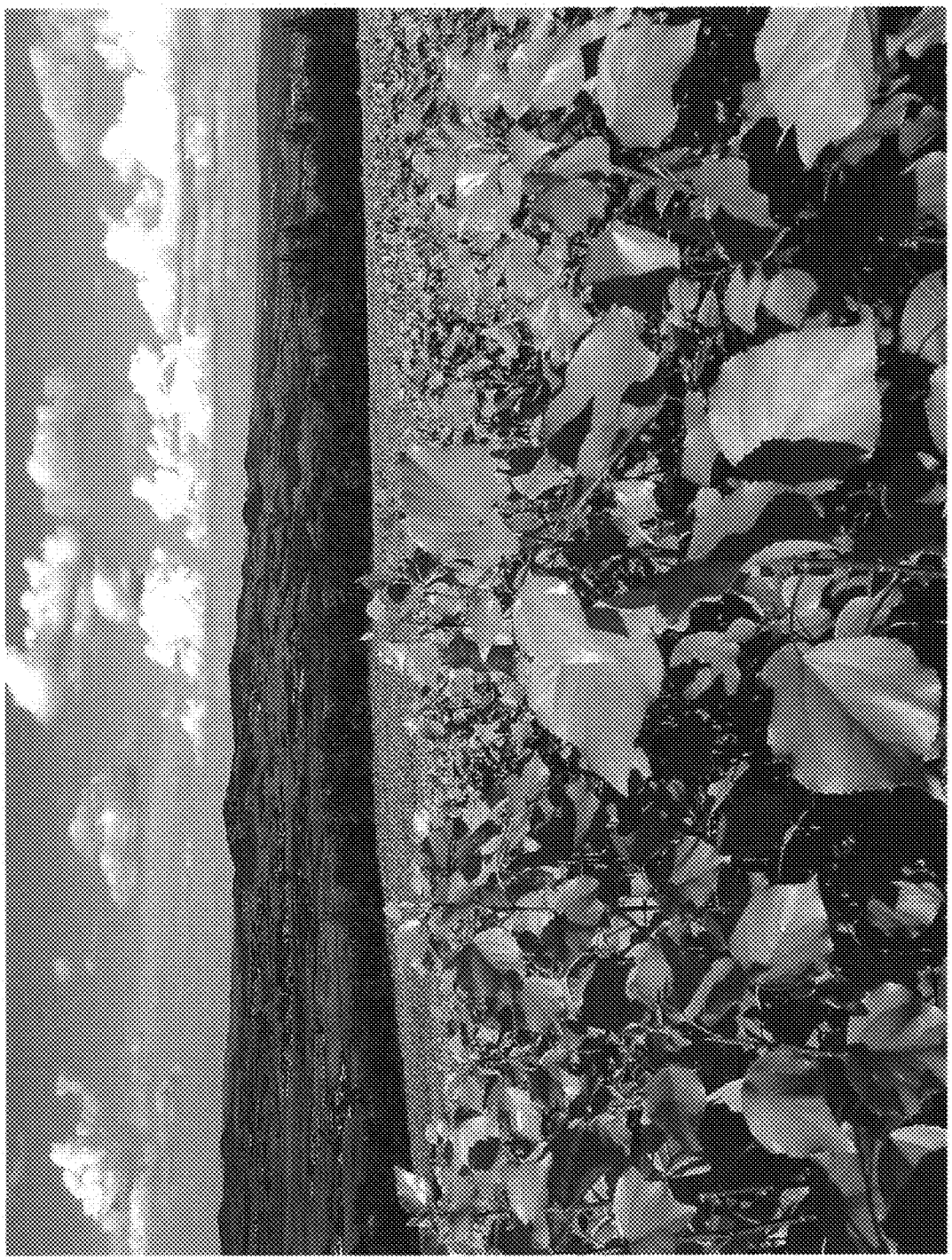
Figure 6:
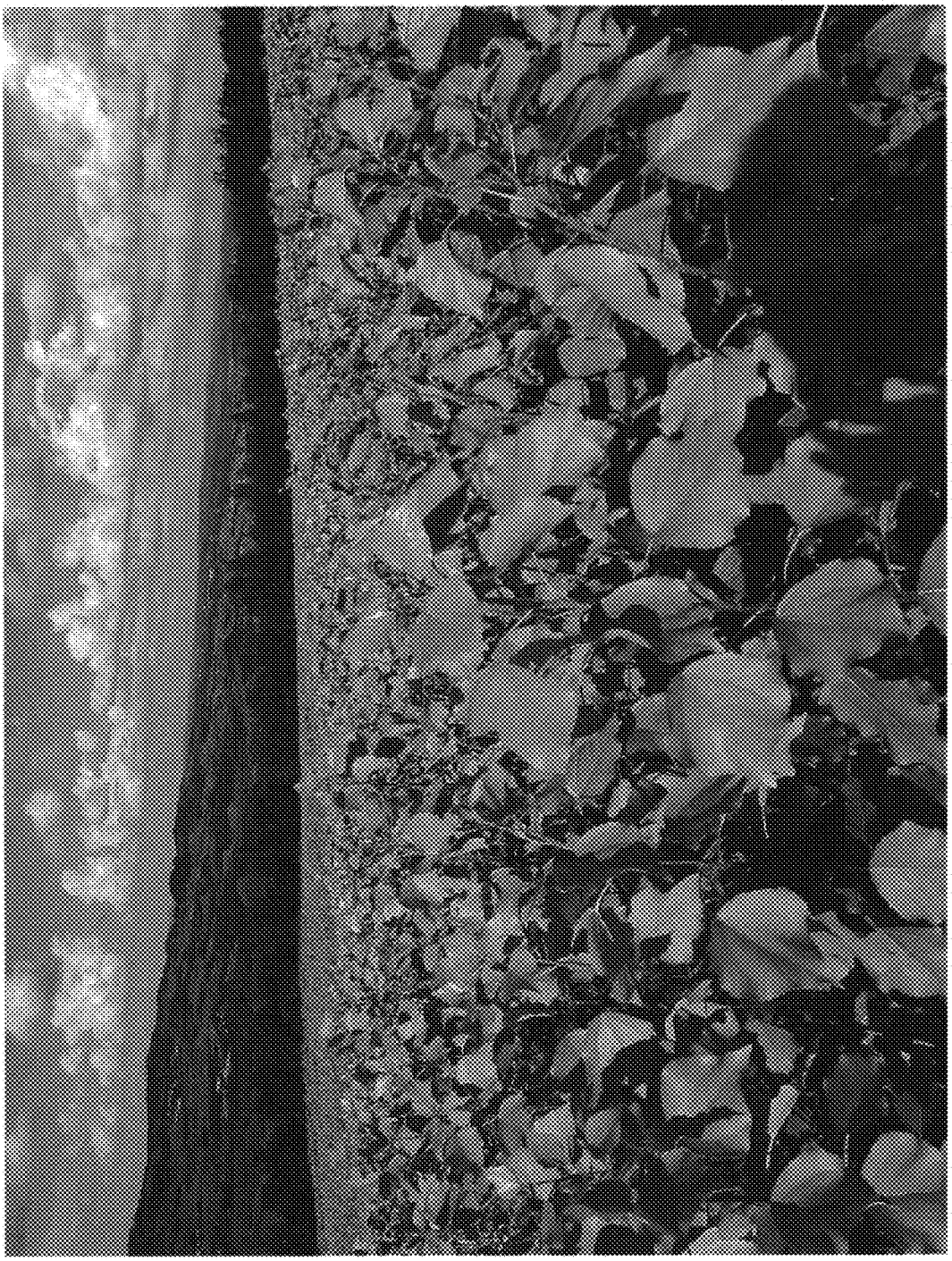
Figure 7:
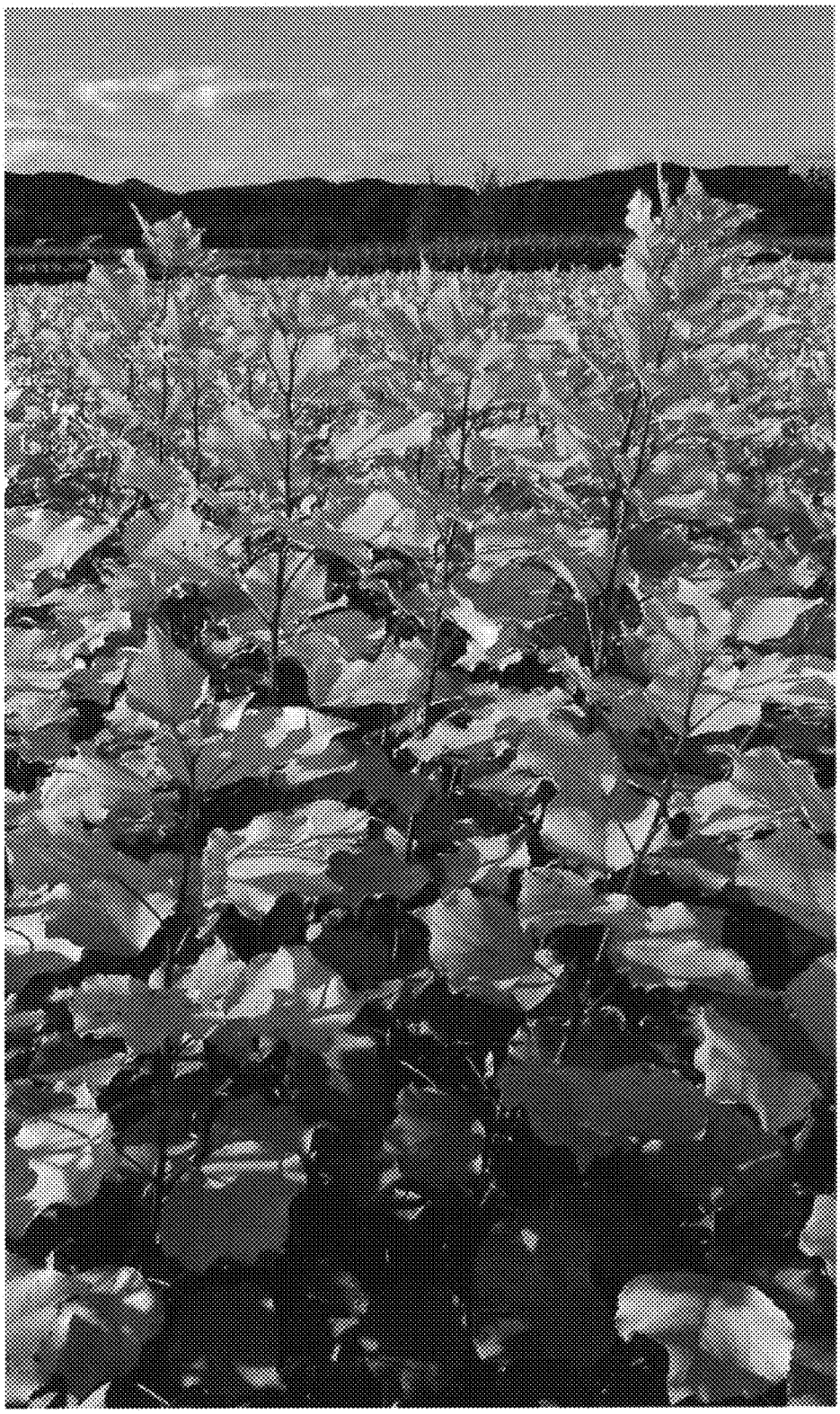
FIGS. 7 and 8 show one-year-old trees with two-year-old roots and one-year old-stem of the new variety 'Gold Poplar' in the summer of 2017 in Huadian, Jilin, China.
Figure 8:
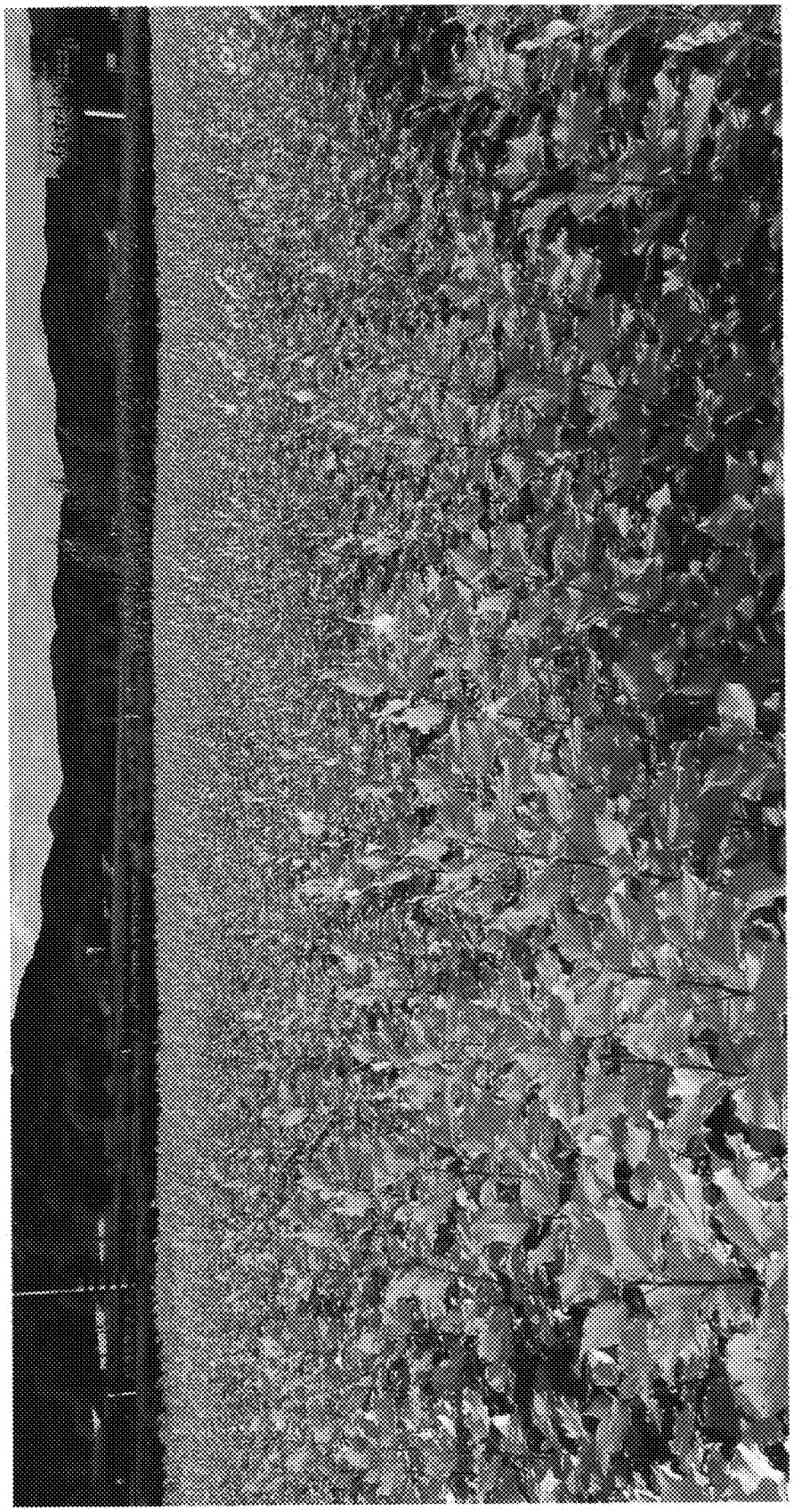

Throughout this specification, color names beginning with a small letter signify that the name of that color, as used in common speech is aptly descriptive. Color number descriptions were obtained using the Complete Process Colour Finder (Art Distribution Center Ltd., 1996).

The descriptive matter which follows pertains to three-year-old 'Gold Poplar' plants grown in Jilin, China and evaluated on Mar. 29, 2018. It is believed to apply to plants of the variety grown under similar conditions of soil and climate elsewhere.

Plant:
- *Growth potential.*—Weak.
- *Shape of trunk.*—Straight.
- *Shape of crown.*—Ovate.
- *Bark cracking.*—Absent (young tree).

Stem:
- *Shape of crown.*—Ovate.
- *Angle on ¾ height stem.*—Present.

Stem:
- *Groove depth on ¾ stem.*—Medium.
- *Color of sunny side on ¾ stem.*—About reddish brown (C30,M80,Y80,K30).
- *Color of nightside on ¾ stem.*—About pale red (C0, M70,Y60,K0).
- *Mucilages on ¾ height stem.*—Present.
- *Floss on ¾ height stem.*—Absent.
- *Angle on ½ height stem.*—Present.
- *Groove depth on ½ stem.*—Shallow.
- *Color of sunny side on ½ stem.*—About light green (C60,M30,Y40,K0).
- *Color of nightside on ½ stem.*—About grey green (C70,M40,Y60,K20).
- *Color of ¾ height stem.*—About reddish brown (C30, M80,Y80,K30).
- *Shade color of ¾ height stem.*—About light red (C0, M70,Y60,K0).
- *Texture of ¾ height stem.*—Edges and grooves present.
- *Cross section at ¾ height at the center of an internode.*—Circular with irregularly distributed with triangular protrusions on the periphery. The number of triangular protrusions is 3 to 6 and the height of the triangular protrusions is 1 cm to 3 cm.
- *Sipules.*—Absent.
- *Time of appearance of green tips of the terminal bud.*—Medium to late.

Lenticels:
- *Distribution.*—Irregular.
- *Shape.*—Circle.

Lateral branch:
- *Quantity.*—Large, about 20 to 25.
- *Angle.*—Medium, about 50 to 70 degrees.
- *Attitude.*—Upward.

Leaf:
- *Leaf glands shape at base of leaf.*—Oval.
- *Leaf posture.*—Upward (spring and summer).

Leaf bud:
- *Shape.*—Long ovate.
- *Length.*—Medium, approximately 4 cm to 6 cm.
- *Color.*—About reddish brown (C30,M80,Y80,K30).
- *Apex shape.*—Acuminate.
- *Way of growing.*—Adhesion.
- *Position in relation to stem.*—Adpressed with divergent tip.

Leaf blade:
- *Color in spring.*—About tender yellow (Y100,C10,M5, B0).
- *Color in summer.*—About yellow-green (Y100,C20, M10,B0).
- *Color in autumn.*—About golden (Y100,C0,M40,B0).
- *Depth of young leaf color.*—Medium.
- *Length.*—Medium, approximately 5 cm to 8 cm.
- *Width.*—Medium, approximately 4 cm to 8 cm.
- *Ratio of midrib length to maximum width of blade.*—0.9-1.1.
- *Anthocyanin in the middle vein of the upper surface.*—Present.
- *Distribution of anthocyanin in middle vein of upper surface.*—From base to middle.
- *Anthocyanin intensity of upper surface midvein.*—Medium.
- *Angle between midrib and second first lateral vein at lower end.*—Approximately 40°-49°.
- *Upper surface villus distribution.*—Absent.
- *Lower surface villus distribution.*—Absent.
- *Surface profile.*—Flat.
- *Degree of concavity and convexity between veins.*—Weak.
- *Base shape.*—Broad wedge.
- *Shape at the junction with petiole.*—Micro concave.
- *Type of tip.*—Short tail tip.
- *Lobes.*—Absent.
- *Margins.*—Regular small serrations with no lobes.

Petiole:
- *Color.*—About red (Y100,M100,C20,K0).
- *Length.*—Medium, approximately 6 cm to 8 cm.
- *Ratio of petiole length to main vein length.*—0.51-0.60.
- *Sectional shape in middle.*—Ellipse.
- *Floss.*—Absent.
- *Upper surface color.*—About red.

Main shoot:
- *Time of termination of growth.*—Early.

Resistance:
- *Insect resistance.*—Medium. The new variety 'Gold Poplar' has shown insect resistance to *Anoplophora glabripennis* motsch (*Anoplopora glabripennis*), Poplar hairy aphid (*Chaitophorus populeti*) and Fall webworm (*Hyphantria cunea*).

*Disease resistance*.—'Gold Poplar' has moderate resistance to black spot disease (*Marssonina castagne*), Poplar canker disease (*Botryosphaeria ribis*), and Poplar leaf rust disease (*Melampsora larici-populina* Kleb).

What is claimed is:

1. A new and distinct variety of poplar tree as herein described and illustrated.

* * * * *